(12) United States Patent
Nakano

(10) Patent No.: US 7,415,256 B2
(45) Date of Patent: Aug. 19, 2008

(54) RECEIVED SIGNAL STRENGTH MEASUREMENT CIRCUIT, RECEIVED SIGNAL STRENGTH DETECTION CIRCUIT AND WIRELESS RECEIVER

(75) Inventor: Yoshiaki Nakano, Osaka (JP)

(73) Assignee: Sharp Kabushiki Kaisha, Osaka-shi, Osaka (JP)

( * ) Notice: Subject to any disclaimer, the term of this patent is extended or adjusted under 35 U.S.C. 154(b) by 397 days.

(21) Appl. No.: 11/210,791

(22) Filed: Aug. 25, 2005

(65) Prior Publication Data

US 2006/0046677 A1   Mar. 2, 2006

(30) Foreign Application Priority Data

Aug. 26, 2004   (JP)   ............... 2004-247318

(51) Int. Cl.
*H04B 17/00* (2006.01)
*H04B 1/10* (2006.01)

(52) U.S. Cl. ............ 455/130; 455/226.2; 455/311; 455/333

(58) Field of Classification Search ... 455/226.1–226.4, 455/67.11–67.7, 333, 307, 311, 314, 338
See application file for complete search history.

(56) References Cited

U.S. PATENT DOCUMENTS

| | | | | |
|---|---|---|---|---|
| 4,247,949 A | * | 1/1981 | Watanabe et al. | ......... 455/226.2 |
| 4,578,820 A | * | 3/1986 | Highton | .................... 455/226.2 |
| 4,680,553 A | * | 7/1987 | Kimura et al. | .................. 330/2 |
| 5,875,390 A | * | 2/1999 | Brehmer et al. | .......... 455/226.2 |
| 5,893,028 A | * | 4/1999 | Brehmer et al. | ............. 455/313 |
| 6,731,918 B1 | * | 5/2004 | Kaneki | ..................... 455/226.1 |
| 7,010,283 B2 | * | 3/2006 | Matsumoto et al. | ...... 455/226.1 |
| 7,054,598 B2 | * | 5/2006 | Bae | .......................... 455/127.2 |
| 7,133,655 B2 | * | 11/2006 | Chiu | ....................... 455/226.4 |

FOREIGN PATENT DOCUMENTS

| | | |
|---|---|---|
| DE | 196 24 391 A1 | 1/1998 |
| JP | 6-140841 | 5/1994 |
| JP | 11-261500 | 9/1999 |
| JP | 2003-46341 | 2/2003 |

* cited by examiner

*Primary Examiner*—Simon D Nguyen
(74) *Attorney, Agent, or Firm*—Birch, Stewart, Kolasch & Birch, LLP

(57) ABSTRACT

The RSSI circuit of the present invention includes: an IF amplifier section, which includes multiple stages of serially connected differential amplifiers for amplifying, with use of a current source IA provided as a power source for amplification, an IF signal corresponding to a received signal; an RSSI amplifier section for converting into current a voltage amplitude of an absolute value signal outputted from the differential amplifiers of the IF amplifier section, using a current source IB provided as a power source for conversion, and adding and outputting the converted current; and a current voltage conversion circuit for converting into voltage the output current from the RSSI amplifier section, and outputting the converted voltage as a measurement voltage value. The RSSI amplifier section is set so that a current value of the RSSI amplifier section is inversely proportional to absolute temperature. With the configuration, it is possible to realize an RSSI circuit, a received signal strength detection circuit and a wireless receiver, which are able to stabilize a strength measurement of a received signal relative to a change in temperature and to increase communication characteristics.

15 Claims, 11 Drawing Sheets

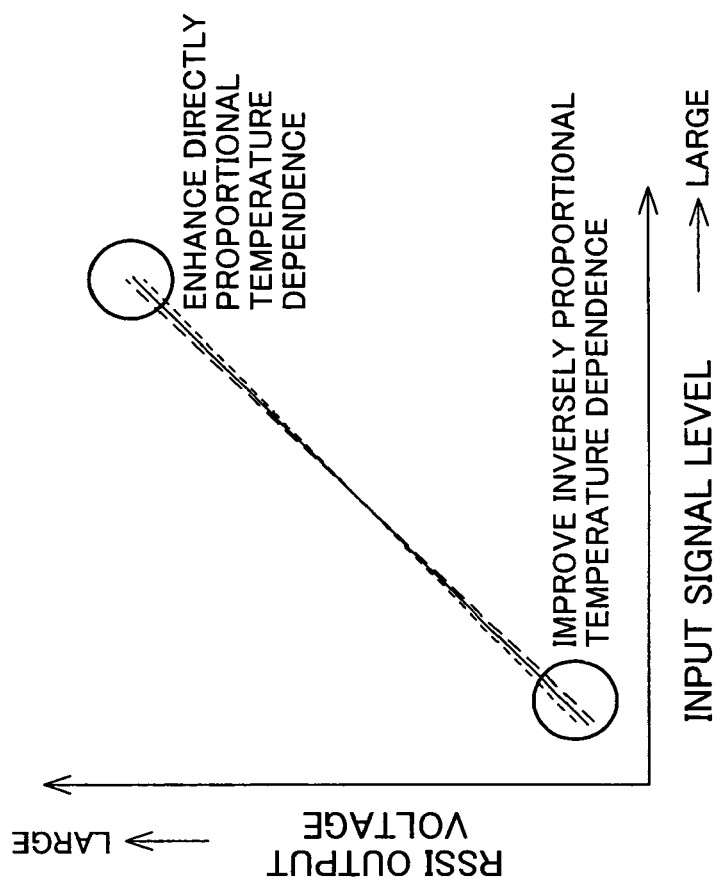
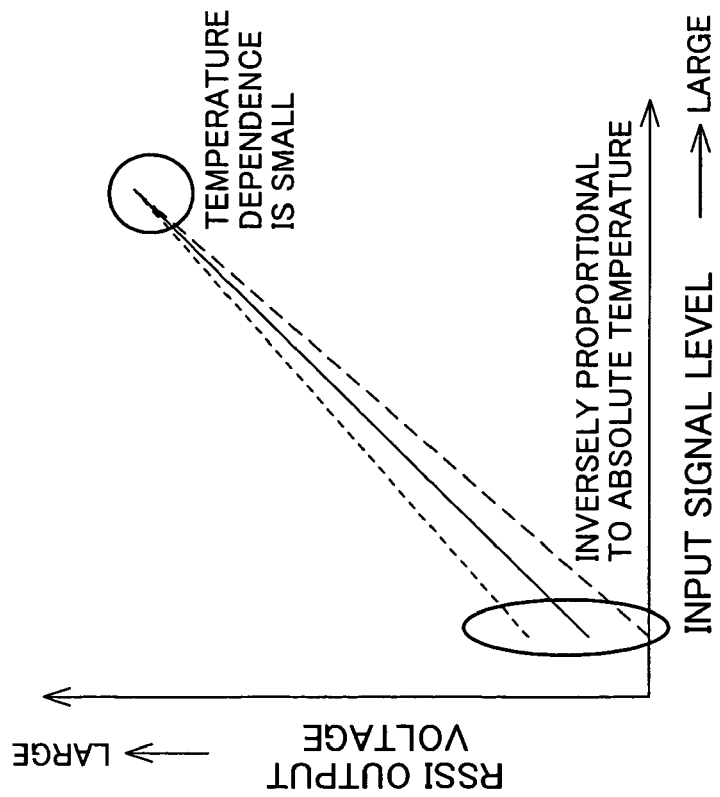

US 7,415,256 B2

RECEIVED SIGNAL STRENGTH MEASUREMENT CIRCUIT, RECEIVED SIGNAL STRENGTH DETECTION CIRCUIT AND WIRELESS RECEIVER

This non-provisional application claims priority under 35 U.S.C. § 119(a) on Patent Application No. 2004/247318 filed in Japan on Aug. 26, 2004, the entire contents of which are hereby incorporated by reference.

FIELD OF THE INVENTION

The present invention relates to a received signal strength measurement circuit (referred to as an RSSI circuit in general) and a received signal strength detection circuit, used for a wireless receiver and having superior temperature stability, and a wireless receiver using the circuits.

BACKGROUND OF THE INVENTION

Generally, in a wireless receiver, a high-frequency radio signal from an antenna is firstly converted into a signal with an intermediate frequency (IF (Intermediate Frequency) signal), and then the IF signal is amplified and inputted to a detector. In the detector, a desired signal process, namely, a detection process in which information included in the radio signal is taken out is performed. In this detection process, the gains of the radio signal and the IF signal are set according to a signal strength of the electric wave received by the wireless receiver, so as to be in a range in which the detection process can be desirably performed.

The signal strength of an electric wave is generally referred to as a received signal strength indicator (RSSI), and measured by an RSSI circuit system.

In portable phones including an IQ modulator/demodulator and the like, an example of the RSSI is a direct current voltage generated by a diode performing envelope detection of a received signal whose band is limited by an IF filter. The RSSI is also used for generating various control signals by being inputted to a base band process circuit.

As illustrated in FIG. 14, an RSSI circuit system using a conventional IF amplifier circuit is primarily constituted of an IF amplifier current source circuit 1210, an IF amplifier circuit 1220, an RSSI amplifier circuit 1230, and a conversion circuit 1240 (see Patent Document 1). These circuits are often integrated in, for example, an LSI (integrated circuit).

The IF amplifier current source circuit 1210 supplies a current to the IF amplifier circuit 1220. The IF amplifier circuit 1220 is made by serially cascading amplifiers 1221, 1222, 1223 and 1224, and amplifies an input signal supplied from, for example, an exterior signal source 1270, and outputs the signal from each stage. The RSSI amplifier circuit 1230 converts voltages outputted from the respective stages of the amplifiers 1221, 1222, 1223 and 1224 in the IF amplifier circuit 1220, and adds up the currents of the respective stages to output an RSSI signal current.

The conversion circuit 1240 converts the RSSI signal current, based on conversion characteristics set by a reference resistance 1250, so as to correct influence of temperature dependence to an extent practically negligible. An output current converted by the conversion circuit 1240 is outputted from an output terminal 1260 to, for example, an external signal strength display device.

Each of the amplifiers 1221, 1222, 1223 and 1224 in the IF amplifier circuit 1220 is, for example, a differential amplifier circuit. To be specific, as illustrated in FIG. 15, the differential amplifier circuit includes load resistors 1321 and 1322, transistors 1323 and 1324, input terminals 1325 and 1326, an output terminal 1327, and a current source 1328. The transistors 1323 and 1324 constitute a differential amplifier. Based on a current supplied from the IF amplifier current source circuit 1210, the current source 1328 outputs a current, which essentially becomes an amplification current source for the transistors 1323 and 1324.

(Patent Document 1) Japanese Laid-Open Patent Application No. 46341/2003 (published date: Feb. 14, 2003)

The current supplied from the IF amplifier current source circuit 1210 varies depending on voltage Vt and inner resistance R. As such, an output from the output terminal 1327 also varies depending on voltage Vt and inner resistance R.

However, when the input level is low and accordingly the amplifiers 1221, 1222, 1223 and 1224 of the respective stages of the IF amplifier circuit 1220 do not saturate, outputs from these amplifiers do not have temperature dependence.

On the other hand, there is a case where the input level is high and accordingly the amplifiers 1221, 1222, 1223 and 1224 of the respective stages of the IF amplifier circuit 1220 saturate sequentially from a later stage to a previous stage. In such a case, the output from each of the amplifiers 1221, 1222, 1223 and 1224 becomes the product of the load resistors 1321 and 1322 and a current from the current source 1328, and shows high (strong) temperature dependence directly proportional to Vt (Vt=kT/q; here, k is a Boltzmann constant, T is absolute temperature, and q is an amount of electrical charge).

As a result, the output of the RSSI amplifier circuit 1230 also varies depending on a change in Vt. The change causes an error in the output from the RSSI circuit system (a result of measurement of received signal strength).

Therefore, in the conventional RSSI circuit system, the output of the RSSI amplifier circuit 1230, which varies depending on Vt, is converted by the conversion circuit 1240 based on conversion characteristics set by the reference resistance 1250, so that the influence of temperature dependence is corrected to an extent practically negligible.

As described above, in the conventional RSSI circuit system, there is a problem that temperature dependence of an output amplitude (gain) varies greatly depending on the input level to the IF amplifier circuit 1220, with the result that output characteristics vary depending on temperature and therefore may cause error. When the input level is low, the amplifiers 1221, 1222, 1223 and 1224 of the respective stages in the IF amplifier circuit 1220 do not saturate. When the input level is high, the amplifiers 1221, 1222, 1223 and 1224 of the respective stages in the IF amplifier circuit 1220 saturate, or almost saturate.

Further, in the conventional RSSI circuit system, there are such problems that in order to solve the problem of temperature dependence of an output, the conversion circuit 1240 is needed and accordingly the whole circuit arrangement becomes complicated. Another problem is that, when the RSSI circuit system is integrated in LSI, an additional space for integrating the conversion circuit 1240 is needed, which makes it difficult to downsize or integrate the circuit. Further, power consumption is increased due to the conversion circuit 1240.

SUMMARY OF THE INVENTION

The present invention was made in view of the foregoing problems, and its object is to provide an RSSI circuit system in which a current source with two kinds of temperature dependence characteristics is used to control temperature dependence of an amplifier, and in which a temperature correction circuit using such a current source is used to suppress or eliminate temperature dependence without using a complicated conversion circuit.

In order to achieve the object, the RSSI circuit according to the present invention includes: an IF amplifier section, which includes multiple stages of serially connected differential amplifiers for amplifying, with use of a first current source provided as a power source for amplification, an IF signal corresponding to a received signal; a voltage-current conversion section for converting into current a voltage amplitude of an absolute value signal outputted from the differential amplifier of each stage of the IF amplifier section, using a second current source provided as a power source for conversion, and adding and outputting the converted current; and a voltage output section for converting into voltage the output current from the voltage-current conversion section, and outputting the converted voltage as a measurement voltage value, the voltage-current conversion section being set so that a current value of the voltage-current conversion is inversely proportional to absolute temperature.

With the arrangement, when the input level is high and the output is saturated, the absolute value signal of each differential amplifier of the IF amplifier section changes directly proportional to a change of absolute temperature.

On the other hand, with the arrangement, the temperature-dependent change of the absolute value signal from the IF amplifier section can be reduced by canceling it out by the voltage-current conversion section, which is set so that the concerted current is inversely proportional to absolute temperature. As a result, with the arrangement, it is possible to stably measure the strength of a received signal relative to a change of temperature.

In order to solve the problem, a received signal strength detection circuit according to the present invention includes the RSSI circuit and a comparator for outputting as a digital signal a result of comparison of an output voltage value of the RSSI circuit and a predetermined reference voltage.

In order to solve the problem, a wireless receiver according to the present invention includes the RSSI circuit or the RSSI detection circuit.

The RSSI detection circuit or the wireless receiver including the RSSI circuit according to the present invention can stably measure the strength of a received signal relative to a change of absolute temperature, so that accuracy of reception can be increased and communication characteristics can be improved.

For a fuller understanding of the nature and advantages of the invention, reference should be made to the ensuing detailed description taken in conjunction with the accompanying drawings.

BRIEF DESCRIPTION OF THE DRAWINGS

FIG. 8($a$) is a graph representing an operation of a temperature correction circuit of the RSSI circuit, showing a case in which the temperature correction circuit makes no correction.

FIG. 8($b$) is a graph representing an operation of the temperature correction circuit of the RSSI circuit, showing a case in which the temperature correction circuit makes correction.

DESCRIPTION OF THE EMBODIMENTS

First Embodiment

Figure 1:
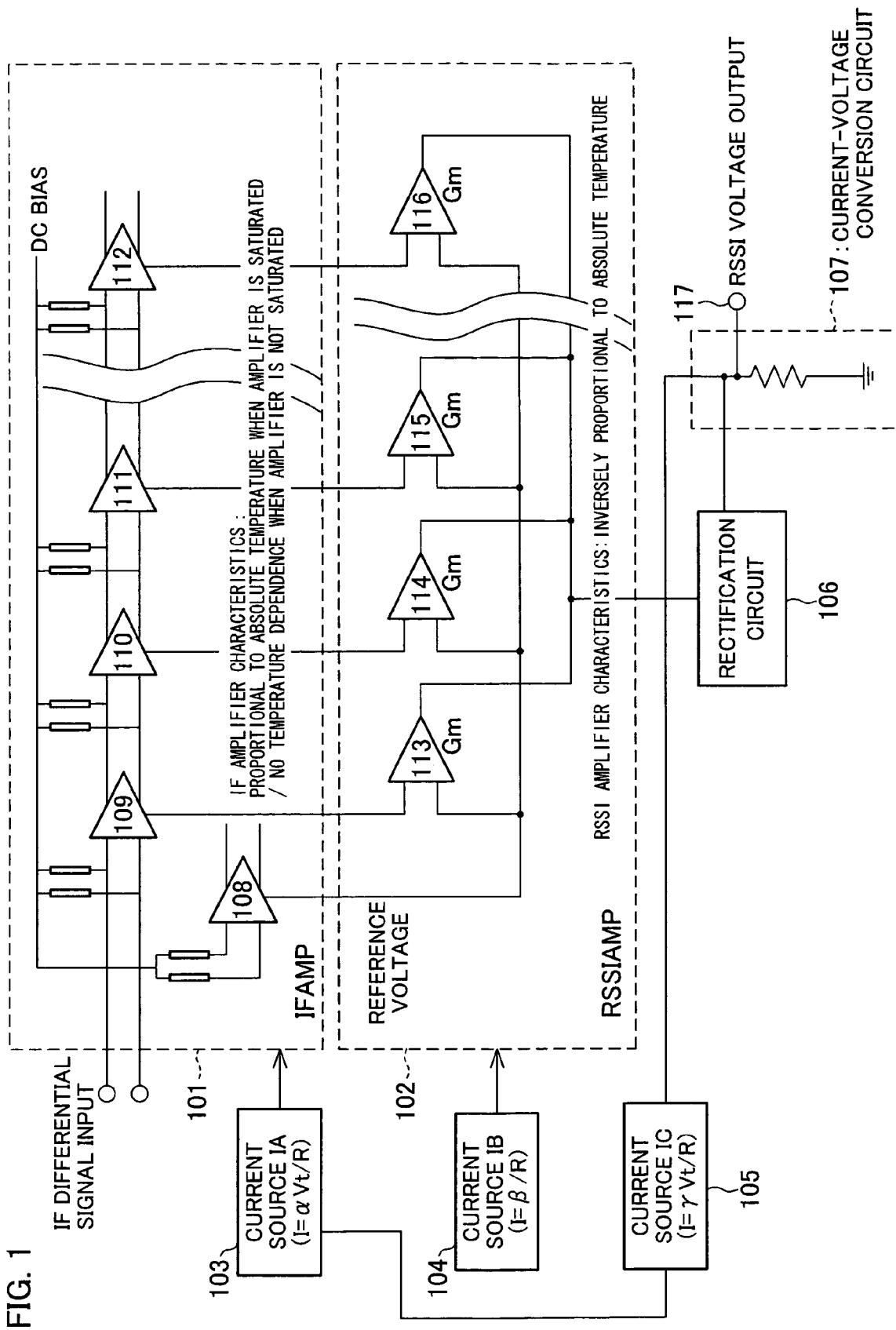
FIG. 1 is a circuit block diagram illustrating a first embodiment of an RSSI circuit according to the present invention.

An embodiment of the present invention is explained below in detail with reference to figures. FIG. 1 represents an embodiment showing an overall structure of an RSSI circuit of the present invention. The RSSI circuit includes an IF amplifier 101, an RSSI amplifier (voltage-current conversion section) 102, a current source IA 103, a current source IB 104, a current source IC 105, a rectification circuit 106, and a current-voltage conversion circuit (voltage output section) 107.

The IF amplifier 101 is constituted by cascading plural stages of amplifiers (differential amplifiers) 109 through 112. Each of the amplifiers 109 through 112 constituting the IF amplifier amplifies an inputted signal and outputs the amplified signal to the amplifier of the next stage.

In addition to an amplifying function, each of the amplifiers 109 through 112 serves to output an absolute value signal of the magnitude proportional to an absolute value of the inputted signal. The absolute value signal of each of the amplifiers 109 through 112 is outputted to the RSSI amplifier 102. Here, in the IF amplifier 101, if the output of the amplifier of a preceding stage is saturated, the output level of the absolute value signal from the amplifier of the next stage is proportional to absolute temperature.

The RSSI amplifier 102 includes a plurality of Gm amplifiers (differential amplifiers). The absolute value signals respectively outputted from the amplifiers 109 through 112 constituting the IF amplifier 101 are inputted to corresponding Gm amplifiers 113 through 116. Further, the RSSI amplifier 102 converts the amplitudes of output voltages of the absolute value signals into currents in the Gm amplifiers 113 through 116, generates an RSSI signal current by adding the current outputs from the respective Gm amplifiers, and outputs the RSSI signal current. The RSSI signal current includes a frequency component (alternating current component, AC component) contained in the input signal.

The rectification circuit 106 removes the AC component from the RSSI signal current, and thereby generates a DC current from the RSSI signal current, and outputs it. The current voltage conversion circuit 107 converts the DC current into a voltage with a resistor provided in the current voltage conversion circuit 107, so as to obtain a measurement voltage according to the signal level inputted to the IF amplifier 101.

The current source IA 103 of the IF amplifier 101 supplies a current that is inversely proportional to a reference resistance R and directly proportional to absolute temperature. The current source IB 104 of the RSSI amplifier 102 supplies a current that is inversely proportional to the reference resistance R and does not depend on absolute temperature. The current source IC 105 supplies a current that is inversely proportional to the reference resistance R and directly proportional to absolute temperature, to the current voltage conversion circuit 107, and serves as a temperature characteristic correction circuit.

Figure 2:
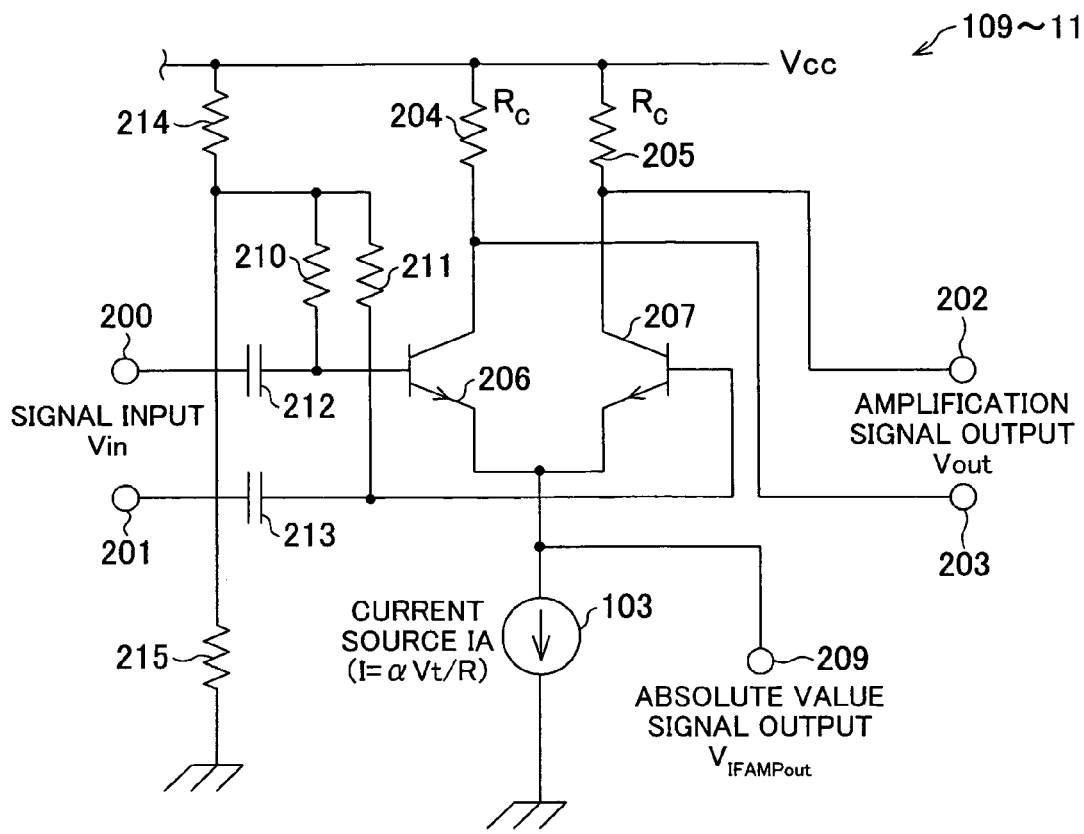
FIG. 2 is a circuit diagram illustrating an example of a differential amplifier constituting an IF amplifier of the RSSI circuit through multi-stage connection.

Next, referring to FIG. 2, the following will describe an example of the amplifiers 109 through 112 constituting the IF amplifier 101 through multi-stage connections. The description is given based on only one of the amplifiers because the amplifiers 109 through 112 all have the same function. As illustrated in FIG. 2, the amplifier is a differential amplifier, and includes input terminals 200 and 201 to which two input signals Vin are respectively inputted, capacitors 212 and 213 for removing the DC component from the input signals Vin, and transistors 206 and 207 to bases of which are supplied AC-component signals obtained by removing the DC component from the input signals Vin.

Further, in the amplifier, the voltages generated by dividing a power supply voltage Vcc with resistors 214 and 215 are respectively supplied as a DC bias to the bases of the transistors 206 and 207 through resistors 210 and 211. The differential amplifier is constituted of resistors 204 and 205, the transistors 206 and 207, and the current source IA 103. Therefore, when the current source for amplifying power is IA, and the load resistances of the amplifier (collector resistances of the transistors 206 and 207, namely, the resistors 204 and 205) are Rc, the gain of the amplifier is expressed by the following equation (1). In equation (1), IA indicates a current of the current source IA.

$$Gain = IA \cdot Rc/(2Vt) \quad (1)$$

(Vt=kT/q, q: the magnitude of charge in Coulomb, k: a Boltzmann constant, T: absolute temperature)

Therefore, the output amplitude Vout of the amplifier when the amplifier is in an unsaturated state is, $$Vout = (IA \cdot Rc/(2Vt)) \cdot Vin.$$

Further, the output amplitude Vout of the amplifier when the amplifier is in a saturated state is, $$Vout = IA \cdot Rc.$$

Here, it is assumed that the current source IA has a characteristic represented by the following equation (2).

$$IA = \alpha \cdot Vt/R \quad (2)$$

($\alpha$: a predetermined constant, R: a reference resistance of a predetermined value, showing the same characteristics (including the temperature characteristic) as the load resistance Rc of the amplifier))

When the current source of the amplifier has the characteristics of IA given by equation (2), the voltage amplitude characteristics of the output signal in an unsaturated state is represented by the following equation (3).

$$Vout = (IA \cdot Rc/2Vt) \cdot Vin = (\alpha \cdot Rc/2R) \cdot Vin \quad (3)$$

The voltage amplitude of the output signal in a saturated state is represented by the following equation (4).

$$Vout = IA \cdot Rc = \alpha \cdot Rc \cdot Vt/R \quad (4)$$

As a result, in equation (3) indicative of an unsaturated state, the term Vt vanishes, and since the resistance Rc and the resistance R showing the same temperature change do not generate any temperature change, Vout does not depend on the change of temperature in the unsaturated state. In the saturated state, as shown by equation (4), the term Vt remains, and accordingly the amplifier, being a differential amplifier, outputs a signal proportional to absolute temperature.

On the other hand, the voltage amplitude of a signal outputted from a terminal 209, i.e., the absolute value signal, is represented by the following equation (5).

$$VIFAMPout = |Vin| \quad (5)$$

From the above, in the case where the amplifier of the preceding stage is saturated, the absolute value signal VIFAMPout outputted to the RSSI amplifier 102 is represented by the following equation (6), and is proportional to absolute temperature.

$$VIFAMPout = |\alpha \cdot Rc \cdot Vt/R| \quad (6)$$

In the case where the amplifier of the preceding stage is not saturated and the amplifier signal input to the preceding stage is Vin, the absolute value signal VIFAMPout is represented by the following equation (7), and does not depend on a change in absolute temperature.

$$VIFAMPout = |\alpha \cdot Rc \cdot Vin/2R| \quad (7)$$

Figure 3:
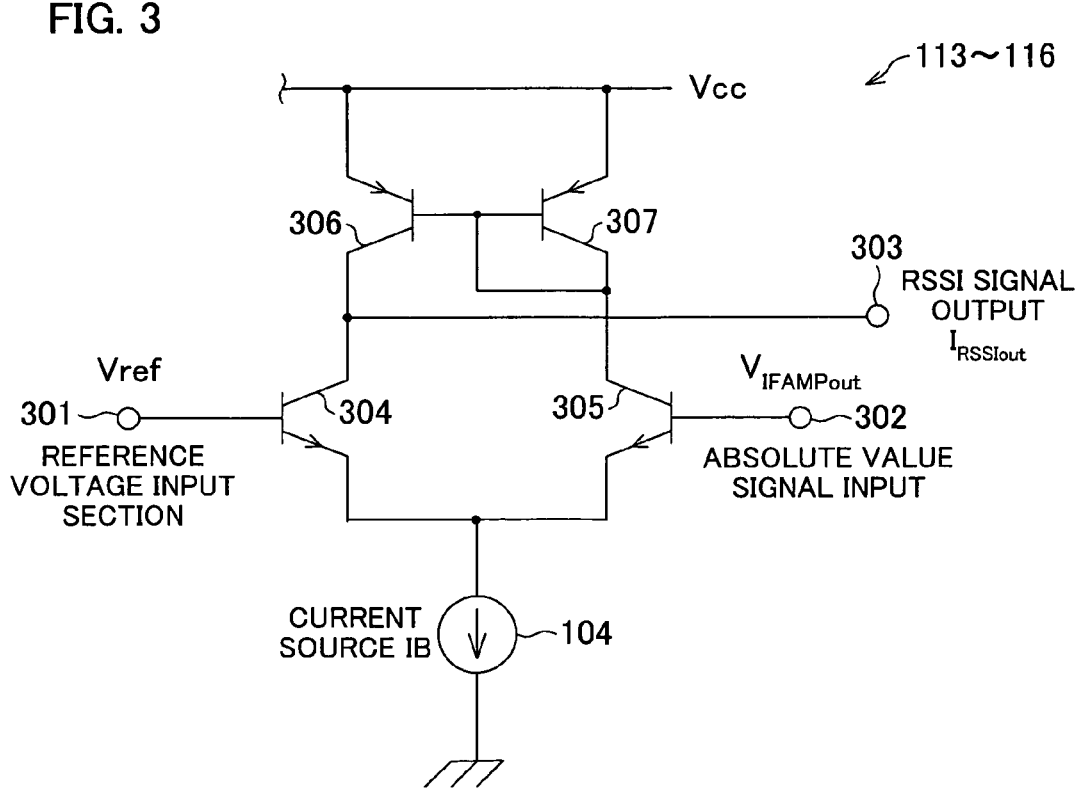
FIG. 3 is a circuit diagram illustrating an example of a differential amplifier constituting an RSSI amplifier of the RSSI circuit.

Next, referring to FIG. 3, the following will describe an example of the Gm amplifiers 113 through 116 provided as differential amplifiers in the RSSI amplifier 102. The description is given based on only one of the amplifier because the Gm amplifiers 113 through 116 all have the same function. The absolute value signal outputted from the IF amplifier 101 is, as illustrated in FIG. 3, supplied to the Gm amplifier through an input 302. Further, a reference voltage equal to the DC voltage included in the IF amplifier output signal is supplied to the Gm amplifier through an input 301.

In the Gm amplifier, the emitters of a pair of transistors 304 and 305 constituting a differential amplifier are connected with each other. The current source IB 104 provided as a power source for amplification is connected with these emitters.

Further, in the Gm amplifier, the input of a current mirror circuit constituted of PNP transistors 306 and 307 is connected with a collector of the transistor 305. On the opposite side, the output of the current mirror circuit is connected, as an active load, with a collector of the transistor 304. Therefore, in the Gm amplifier, a signal generated by voltage-current conversion of a voltage amplitude of the input absolute value signal to a current is outputted from an output 303 connected to the output of the current mirror circuit.

When the input signal to the Gm amplifier constituting the RSSI amplifier 102 is VIFAMPout, the output current from the RSSI amplifier 102 is IRSSIAMPout, and the current of the current source IB 104 is IB, then IRSSIAMPout is represented by the following equation (8).

$$IRSSIAMPout = IB \cdot VIFAMPout/2Vt \quad (8)$$

It is assumed here that the current source IB 104 for amplifying power to the RSSI amplifier 102 is a current source represented by equation (9) below. Vconst is a reference voltage that does not depend on temperature.

$$IB = \gamma \cdot Vconst/R \quad (9)$$

In consideration of IB, IRSSIAMPout is given by $$IRSSIAMPout = \gamma \cdot Vconst \cdot VIFAMPout/(2Vt \cdot R) \quad (10).$$

As a result, the output of the RSSI amplifier 102 becomes inversely proportional to absolute temperature, provided that the reference resistance R does not have temperature characteristics. By replacing $\gamma \cdot Vconst \cdot VIFAMPout/(2R)$ with a constant $\beta$, equation (10) becomes equivalent to the equation of IB shown in FIG. 1.

Next, an embodiment of a reference voltage forming circuit 108 is explained below with reference to FIG. 4. An absolute value signal including a DC voltage component and outputted from the IF amplifier 101 is applied to one input terminal of each Gm amplifier of the RSSI amplifier 102. As a result, there is such a disadvantage that a current cannot be accurately obtained from the absolute value signal unless a reference voltage including completely the same DC voltage as the DC voltage component is also applied to the other input terminal.

Figure 4:
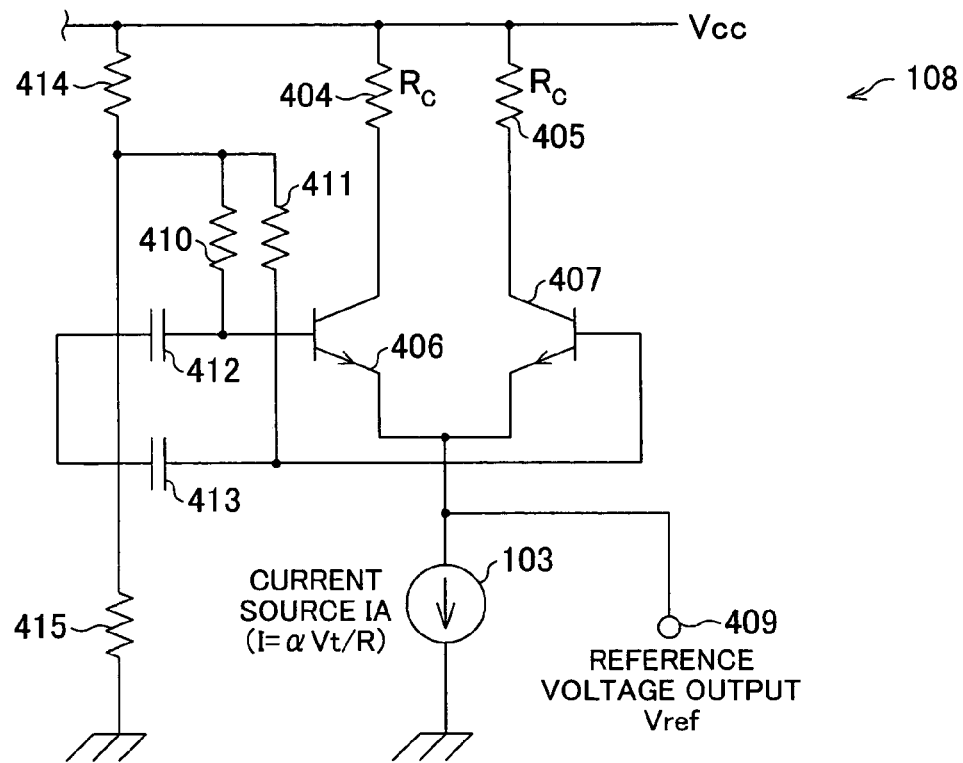
FIG. 4 is a circuit diagram illustrating an example of a reference voltage forming circuit of the RSSI circuit.

In order to eliminate such a disadvantage, as illustrated in FIG. 4, the reference voltage forming circuit 108 has a configuration in which the input section of the amplifier illustrated in FIG. 2 is short-circuited, and the output section is omitted. Further, exactly the same constant is set for the amplifiers 109 through 112 of the IF amplifier 101, and devices used in this reference voltage forming circuit 108.

As a result, the output section (emitters of the transistors 206 and 207) of the amplifier and the reference voltage forming circuit (emitters of transistors 406 and 407) 108 can have substantially the same DC potential fluctuations even if there is a characteristic change in the devices due to a temperature change or lot variations.

Figure 5:
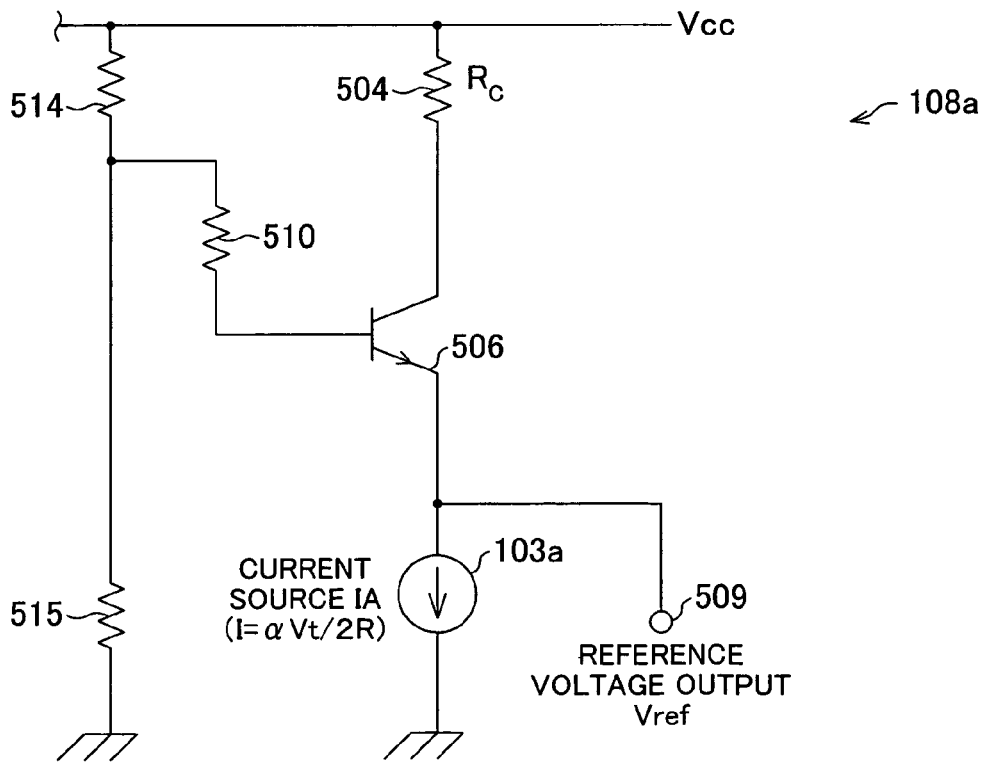
FIG. 5 is a circuit diagram illustrating another example of the reference voltage forming circuit of the RSSI circuit.

Next, another embodiment of the reference voltage forming circuit 108 is explained below as a reference voltage forming circuit 108a, with reference to FIG. 5. As illustrated in FIG. 5, the reference voltage forming circuit 108a is provided as a differential semi-circuit by omitting the resistor 405, the transistor 407, the capacitors 412 and 413, and the resistor 411 from the reference voltage forming circuit 108 illustrated in FIG. 4, and by setting the current of a current source 103a half the current of the current source 103. Because the base current of a transistor 506 is reduced in half from the circuit illustrated in FIG. 4, resistors 514 and 515 whose resistances are set twice as large as those of the resistors 414 and 415 are used instead of the resistors 414 and 415, taking into consideration a voltage drop in the resistor 515. As a result, the output value of the reference voltage outputted from the reference voltage forming circuit 108a illustrated in FIG. 5 and the output value of the reference voltage outputted from the reference voltage forming circuit 108 illustrated in FIG. 4 can be made equal to each other.

Figure 6:
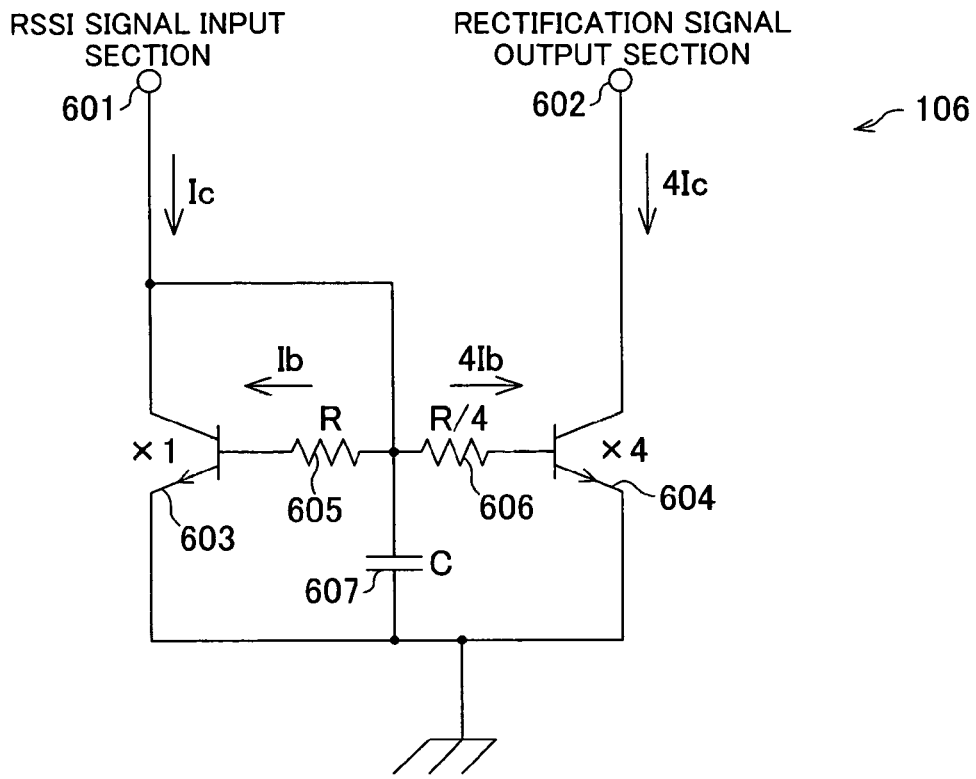
FIG. 6 is a circuit diagram illustrating an example of a rectification circuit of the RSSI circuit.

Next, an example of the rectification circuit 106 is explained below with reference to FIG. 6. As illustrated in FIG. 6, in the rectification circuit 106, an RSSI current (IRSSIAMPout, denoted as Ic in FIG. 6) supplied from an input section 601 is diverged into a collector current for a transistor 603 and base currents for transistors 603 and 604. Here, an area ratio of emitters in the transistors 603 and 604 is set as 1:4.

When the current gain hfe of the transistors 603 and 604 is low, a base voltage drop due to a difference in base currents cannot be ignored. In order to correct this, suitable base resistances are inserted to the bases of the transistors 603 and 604, so as to compensate for the base current. Further, in the rectification circuit 106, a primary LPF (Low Pass Filter) is formed by adding a rectification capacitor 607, so as to remove an alternating current component of the current outputted from an output section 602 (denoted as 4Ic in FIG. 6).

Figure 7:
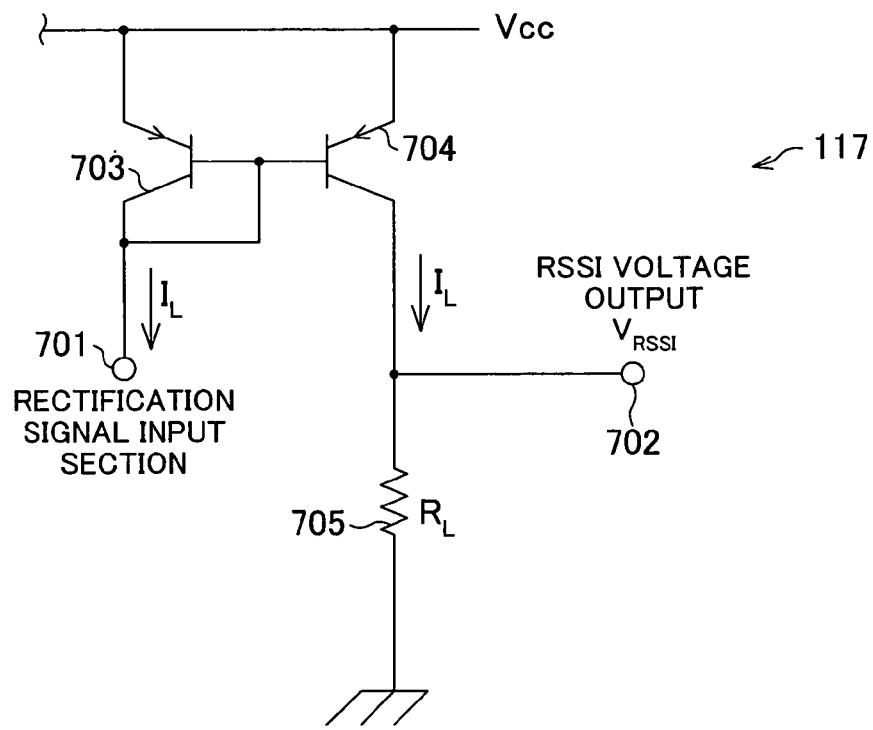
FIG. 7 is a circuit diagram illustrating an example of a current-voltage conversion circuit of the RSSI circuit.

Next, an example of the current-voltage conversion circuit 107 is explained below with reference to FIG. 7. As illustrated in FIG. 7, in the current-voltage conversion circuit 107, a current supplied from the rectification circuit 106 through an input section 701 is inputted to a current mirror circuit constituted of transistors 703 and 704, which then supply an equivalent current to a resistor 705. A voltage generated at the current input-terminal of the resistor 705 is outputted, as an RSSI voltage, through an output terminal 702 for measuring the voltage.

The RSSI output voltage VRSSI is given by $$VRSSI = RL \times IL \quad (11)$$

Here, IL is the current obtained by rectifying the RSSI output current by the current circuit 106. It follows from this that, in the examples of FIGS. 3 and 6, VRSSI is given by $VRSSI = 4 \cdot \gamma \cdot Vconst \cdot RL \cdot VIFAMPout/(2Vt \cdot R) \ldots (12)$ Here, when RL of the current-voltage conversion circuit 107 and the reference resistor R forming the reference current source of the RSSI amplifier 102 are of the same kind (having the same temperature characteristic) formed on the same LSI, changes in the characteristics of the RSSI circuit caused by resistor-induced temperature change or lot variations can be cancelled for improved accuracy.

Next, FIG. 8 represents a graph for describing the function of the current source IC 105 as a temperature correction circuit. In the present embodiment, the RSSI voltage has such a characteristic that the voltage increases with increase in input level. Note that, the effects of the present invention can also be obtained even when the RSSI voltage has such a characteristic that the voltage decreases with increase in input level.

First, without the temperature correction circuit, the input level versus RSSI voltage characteristics is such that, as illustrated in FIG. 8(a), the RSSI output voltage has small temperature dependence for a high input level, and large temperature dependence for a low input level.

Namely, when the input level is high, most of the amplifiers in the IF amplifier 101 saturate, and therefore the output from the IF amplifier 101 is proportional to absolute temperature. However, because the RSSI amplifier 102 and subsequent devices have characteristics inversely proportional to absolute temperature, these characteristics are canceled out at least partially, and accordingly the temperature dependence of the RSSI output voltage is small. On the other hand, when the input level is low, the number of saturated amplifiers is reduced, and therefore temperature dependence of the IF amplifier output is small. However, since the characteristic of the RSSI amplifier 102 and subsequent devices remain essentially the same and are inversely proportional to absolute temperature, the temperature dependence of the RSSI voltage becomes more inversely proportional to absolute temperature, and accordingly the temperature dependence becomes large.

Next, when the temperature correction circuit is provided and a minute correction current proportional to absolute temperature is applied, the input level versus RSSI voltage characteristics take the form as illustrated in FIG. 8(b). With the resistor RL of the current voltage conversion circuit 107 applied with the minute correction current (preferably, no more than half the maximum RSSI current at room temperature, or more preferably with a minimum of 2% or more preferably 4% and a maximum of 10% or more preferably 7% of the maximum RSSI current at room temperature), the temperature characteristics become more proportional to absolute temperature for a high input level, and less inversely proportional to absolute temperature for a low input level.

As to the influence of the minute correction current on the temperature characteristic, applying the correction current whose temperature characteristic depends on absolute temperature greatly improves the temperature characteristic when the input level is small, because in this case the RSSI amplifier 102 in an unsaturated state outputs small current. On the other hand, when the input level is large, in which case the RSSI amplifier 102 outputs large current, applying the minute correction current proportional to absolute temperature does not change the temperature characteristic much.

By thus optimizing the correction current, a gain or loss due to temperature dependence of the RSSI output voltage within an operational range can be reduced.

As to a specific range of the minute correction current, specific numbers cannot be given definitively because it depends on various factors such as a current, a gain, a resistance, temperature and an input level. However, the minute correction current can exhibit its effect if it is within the foregoing range. Further, the range of the minute correction current can be expressed by mathematical formulae as follows.

Figure 9:
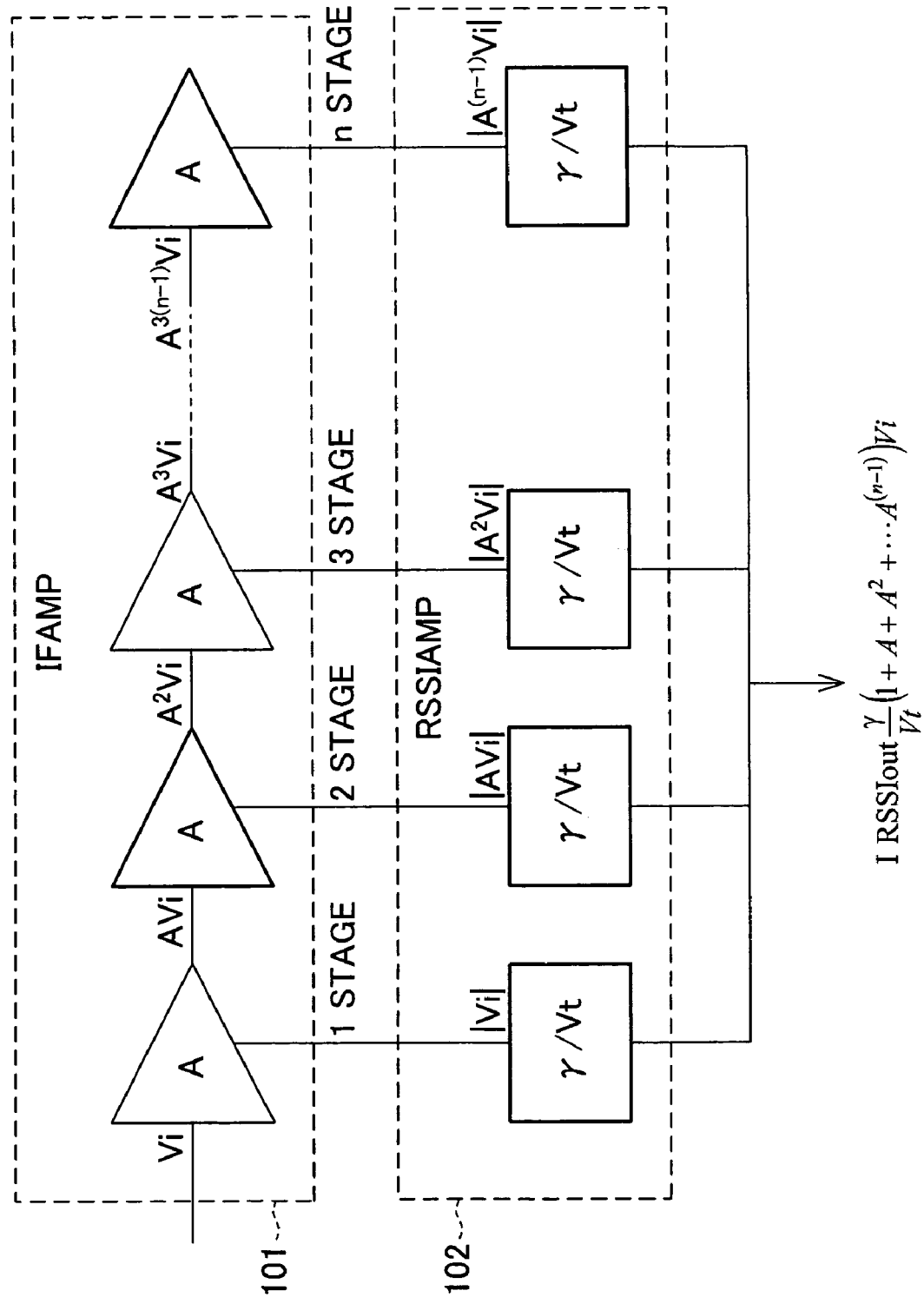
FIG. 9 is a circuit block diagram explaining a minute correction current in the RSSI circuit.

As illustrated in FIG. 9, assume that the IF amplifier 101 is constituted of n stages, and a gain of each stage of the IF amplifier 101 in an unsaturated state is A. In this case, if the input level is low (all the amplifiers are in the unsaturated state), the IRSSIout, which is the sum of the output currents of the RSSI amplifier 102 is represented by the following equation $$IRSSIout = \gamma(1+A+A2+\ldots+A(n-1))Vi/Vt.$$

Figure 10:
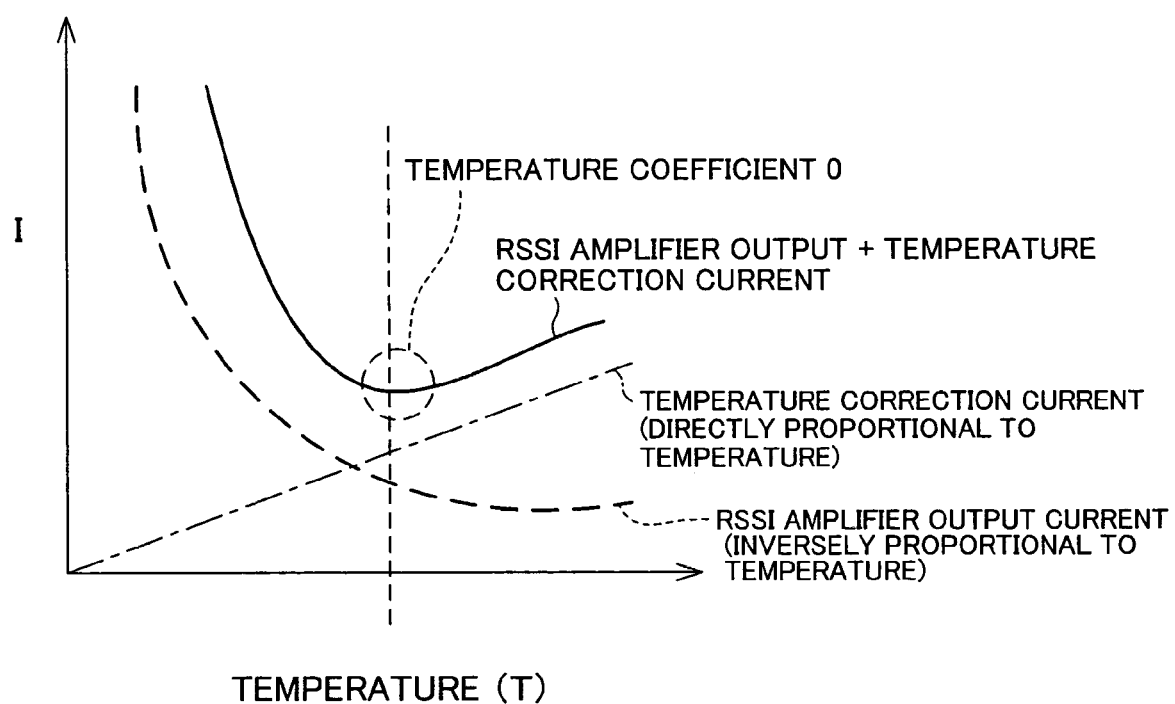
FIG. 10 is a graph representing an optimal value of the minute correction current in a mathematical expression.

Since A and γ are fixed values, the equation can be simplified to IRSSIout=η·Vi/T (where T is absolute temperature). The temperature characteristic correction current is represented by Iadj=BT. As illustrated in FIG. 10, in order to minimize the temperature dependence of the RSSI circuit output voltage in a low input level, the value of Iadj should be set so that the temperature characteristic of IRSSIout+Iadj becomes minimum.

For that purpose, when IRSSIout+Iadj=(η·Vi/T)+BT is differentiated with respect to T, it becomes B−(η·Vi·Vi/T²). Here, when B is set so that a differential coefficient is 0 in a desired minimum input level and at an intermediate temperature in a desired operational temperature range, the temperature characteristic within the operational temperature range becomes minimum. As a result, the optimal value of the temperature correction current is B=(η·Vi/T²). As is clear from FIG. 10, the set value of the temperature correction current value should be within ±20%, or more preferably ±10% of the optimal value.

Figure 11:
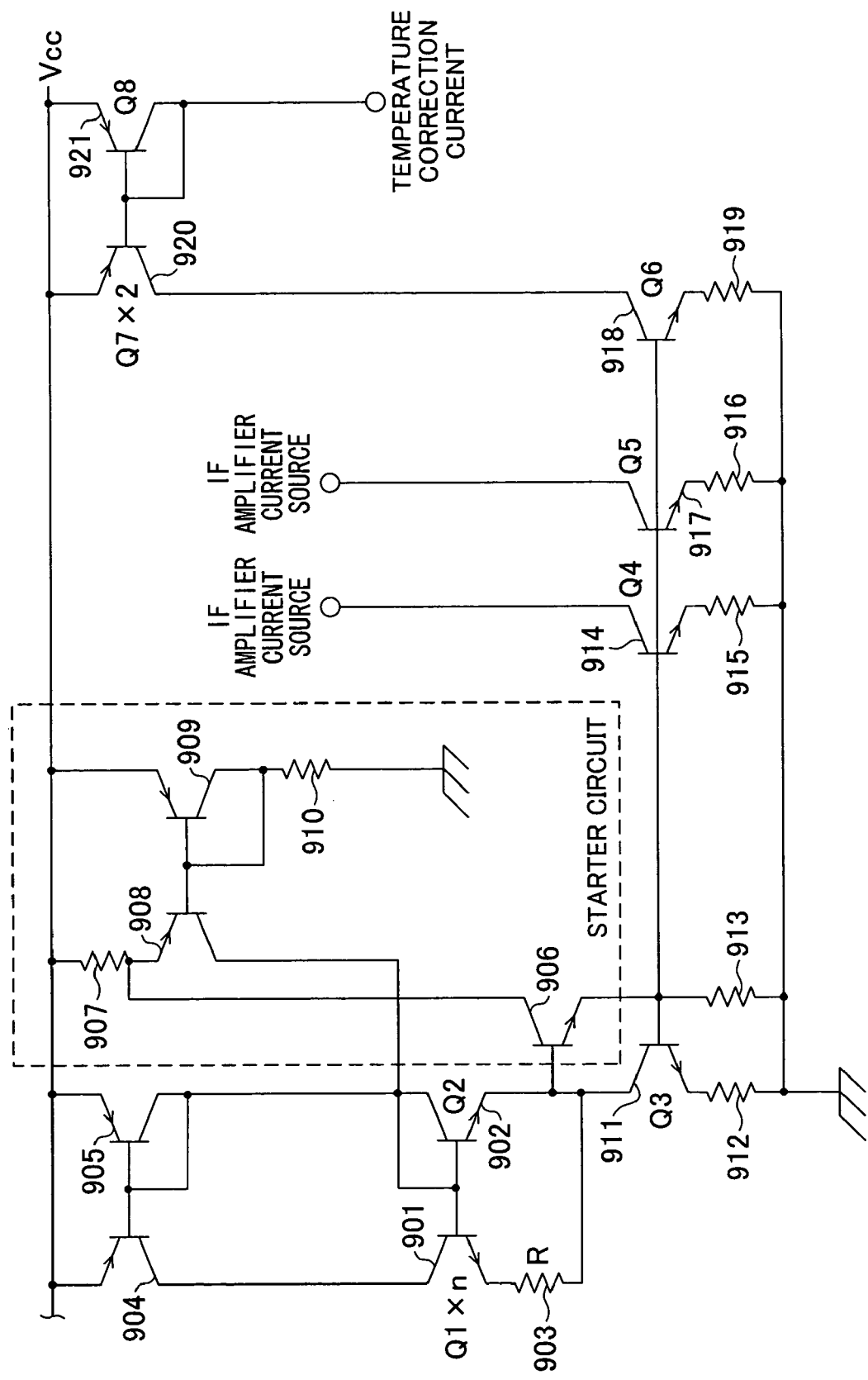
FIG. 11 is a circuit diagram illustrating an example of a correction current source of the temperature correction circuit, and a current source of the IF amplifier.

Next, an example of the current source IC 105 used as the temperature correction circuit, and the current source IA 103 for the IF amplifier 101 is explained below with reference to FIG. 11. As illustrated in FIG. 11, a circuit constituted of transistors 906, 908 and 909, and resistors 907 and 910 is a starter circuit for a current output band gap circuit. The current output band gap circuit is formed of transistors 901, 902, 904 and 905, and a resistor 903. Note that the transistor 901 may be arranged so that n units of transistors 901 (n is an integer of one or greater) are connected in parallel with one another.

Therefore, a collector current (Ic (Q1)) of the transistor 901 (Q1) of the current output band gap circuit is represented by the following equation (13). The resistor 903 is a reference resistor R.

$$Ic(Q1)=Ic(Q2)=(Vt/R)\ln n \qquad (13)$$

Output currents of Q 4 and Q 5 are Ic (Q 4)=Ic (Q5)=Ic (Q1)+Ic (Q2). It follows from this that $$Ic(Q4)=Ic(Q5)=Ic(Q6)=2(Vt/R)\ln n.$$

On the other hand, the current which flows through Q8 becomes (½) Ic (Q6), because two elements Q7, making up the current mirror circuit with Q8, are connected in parallel with each other.

As a result, the power amplifying current and temperature compensating current supplied to the IF amplifier 101 are inversely proportional to the reference resistor R, and directly proportional to absolute temperature.

Here, when the load resistor Rc of the IF amplifier 101 and the output load resistor RL of the rectification circuit 106 are of the same kind (have the same temperature characteristic) as the reference resistor R, the voltage generated through Rc and the voltage generated through RL do not depend on a change in temperature of the resistance or lot variations, as the Ohm's law V=IR indicates, and at the same time, the current source circuit and the correction current source circuit can be combined together. As a result, the circuit can be downsized.

Figure 12:
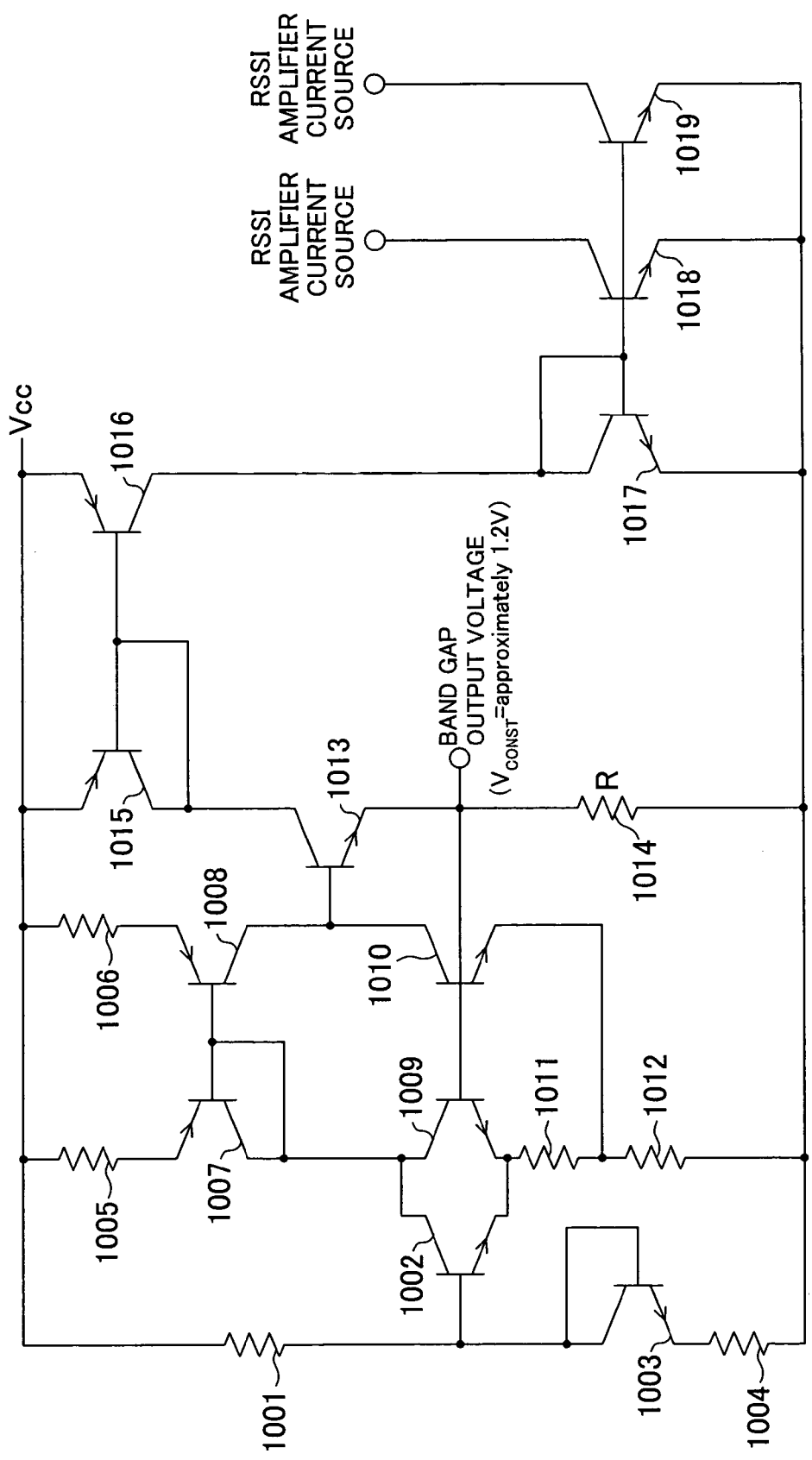
FIG. 12 is a circuit diagram illustrating an example of a current source of the RSSI amplifier of the RSSI circuit.

Next, an example of the current source IB 104 of the RSSI amplifier 102 is explained below with reference to FIG. 12. In the current source IB, a circuit constituted of resistors 1001 and 1004, and transistors 1002 and 1003 is a starter circuit of a voltage output band gap circuit. The voltage output band gap circuit is formed of resistors 1005, 1006, 1011, 1012 and 1014, and transistors 1007, 1008, 1009, 1010 and 1013, and a band gap output voltage is approximately 1.2 V. A current value of the RSSI current source IB 104 is represented by the following equation (14), where Vconst is the band gap voltage, and R is the reference resistance R shown in the resistor 1014.

$$IB=Vconst/R \qquad (14)$$

As a result, the current source IB for supplying current to the RSSI amplifier 102 can output current which is inversely proportional to the reference resistance R and does not depend on absolute temperature.

Figure 13:
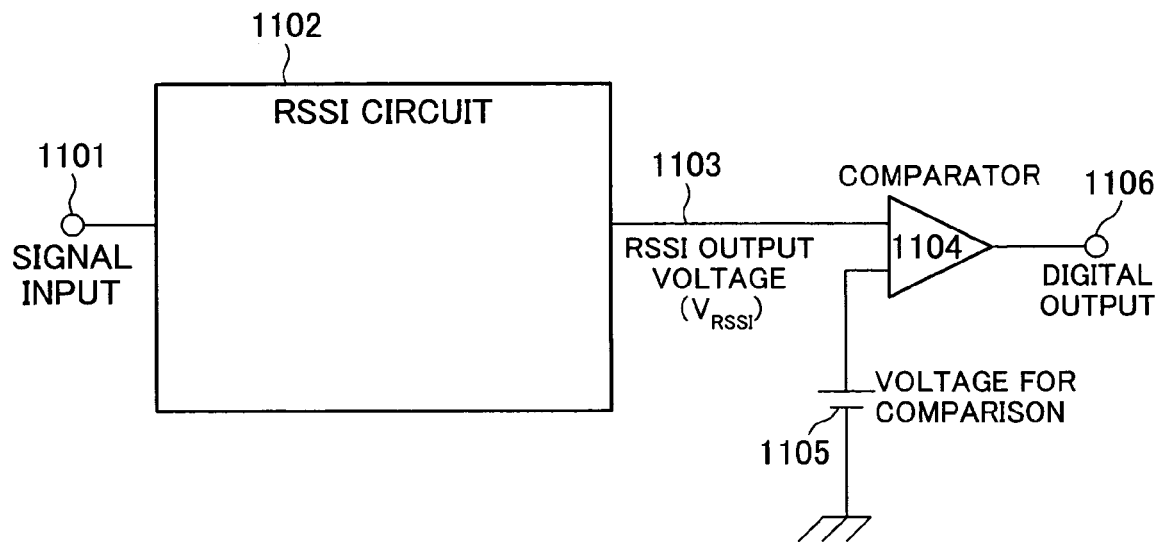
FIG. 13 is a circuit block diagram illustrating an RSSI detection circuit of the present invention.
Figure 14:
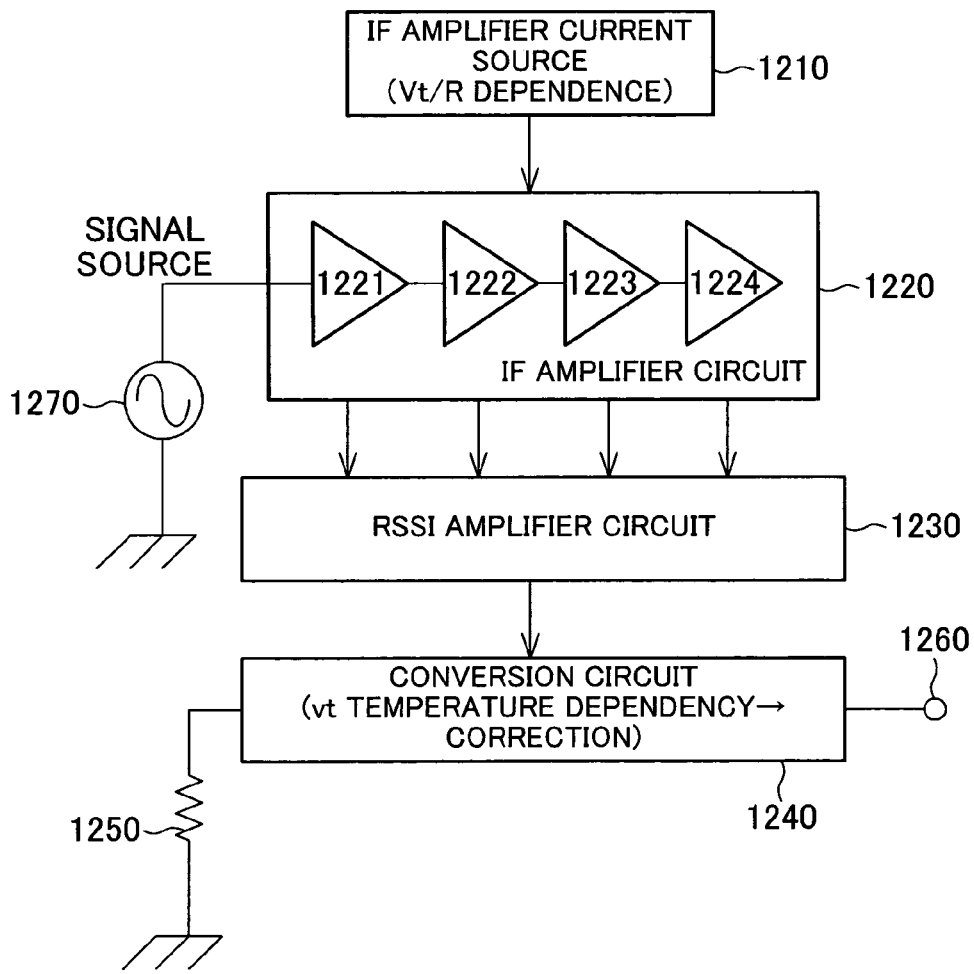
FIG. 14 is a circuit block diagram illustrating a schematic arrangement of a conventional RSSI circuit system.
Figure 15:
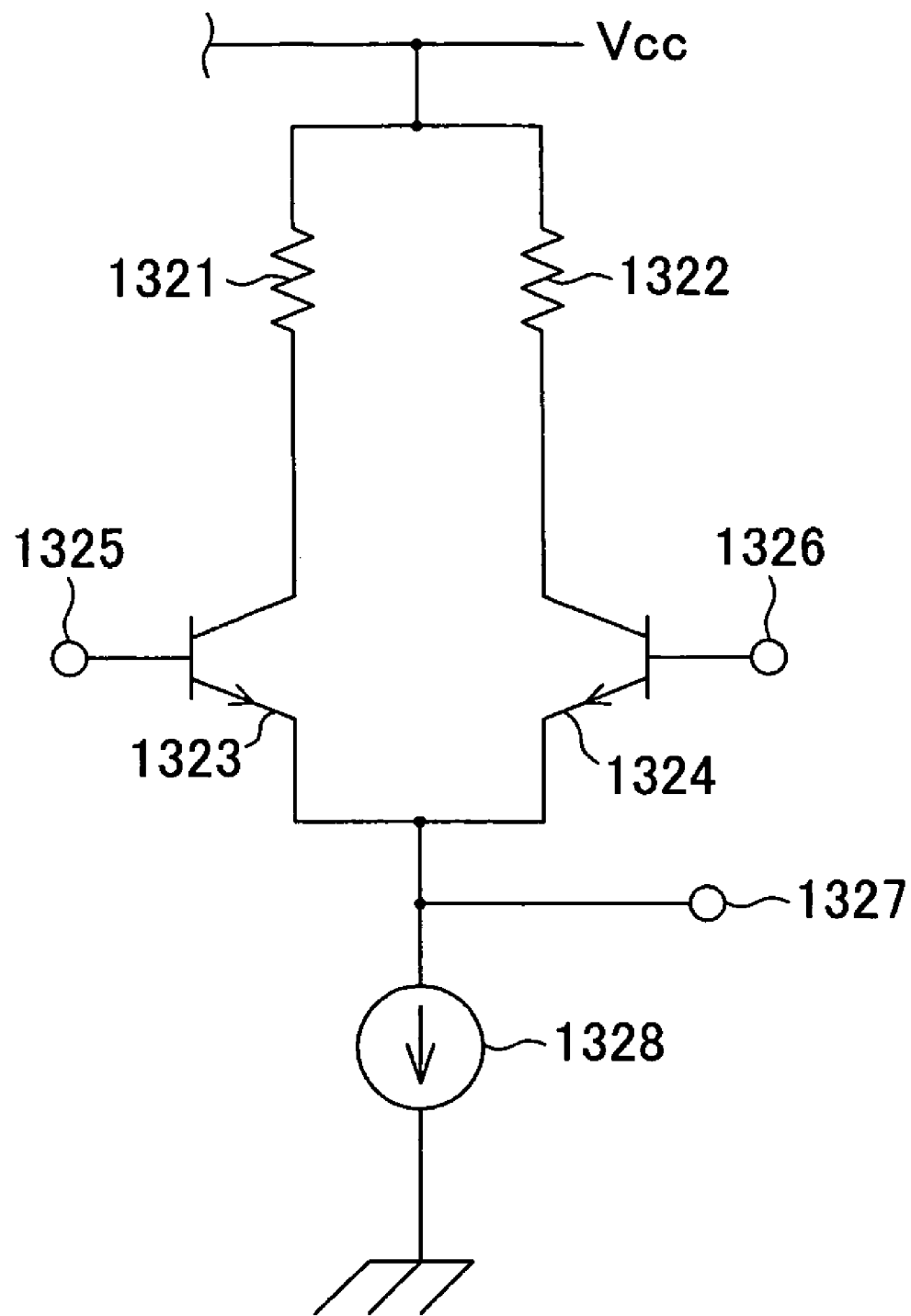
FIG. 15 is a circuit diagram illustrating a circuit arrangement of a main part of each amplifier included in an IF amplifier circuit of a conventional RSSI circuit system.

As illustrated in FIG. 13, in the RSSI detection circuit of the present invention, a signal inputted from a signal input 1101 causes an RSSI circuit 1102 to output a power-dependent voltage through an output line 1103. The output voltage is compared with a predetermined reference voltage 1105 by a comparator 1104, and the result of comparison is outputted as a digital value. In this way, whether the value is greater or smaller than a power value set by the arbitrary reference voltage 1105 can be detected and displayed.

The RSSI circuit of the present invention is a circuit for outputting a voltage proportional to an input signal power, including: an IF amplifier section, which includes multiple stages of serially connected differential amplifiers for amplifying an IF signal; an RSSI amplifier section for converting into current a voltage amplitude of an absolute value signal outputted from the differential amplifier of each stage of the IF amplifier section; a rectification circuit for rectifying a current outputted from the RSSI amplifier section; and a temperature characteristic correction circuit for correcting temperature error, wherein output voltage amplitude of the absolute value signal in a saturated state in the IF amplifier section is proportional to absolute temperature and output voltage amplitude of the absolute value signal in an unsaturated state does not depend on absolute temperature, Gm amplifier of the RSSI amplifier section is inversely proportional to absolute temperature, and thereby a change of the temperature characteristic generated in the IF amplifier section is cancelled by a change of the temperature characteristic of the RSSI amplifier section, so that main temperature dependence is suppressed.

Each differential amplifier of the IF amplifier section may be arranged so that emitters of a pair of transistors are connected with each other, a current source provided as a power source for amplification is further connected with these emitters, a power supply is connected with each collector of a pair of the transistors through a load resistor, the emitters of a pair of the transistors are made an absolute value signal output, the current source provided as a power source for amplification outputs a current whose value is inversely proportional to a reference resistor, the reference resistor and the load resistor are of the same kind, and thereby the outputted current is substantially proportional to absolute temperature.

Further, each differential Gm amplifier of the RSSI amplifier section may be arranged so that emitters of a pair of transistors are connected with each other, a current source provided as a power source for conversion is further connected with these emitters, an input of a current mirror circuit is connected with one of collectors of the transistors and an output of the current mirror circuit is, as an active load, connected with the other collector of the transistors, the output of the current mirror circuit is made a Gm amplifier output, bases of the transistors are made inputs of the Gm amplifier, and thereby Gm amplifier of the RSSI amplifier section is inversely proportional to absolute temperature unless the current source of the RSSI amplifier section does not depend on a change of temperature.

It may be that a predetermined reference DC voltage supplied for removing influence of a DC potential of the IF amplifier section inputted to each Gm amplifier of the RSSI amplifier section is made by a circuit identical in circuit structure with the IF amplifier section and is supplied from a node corresponding to a signal output terminal of the IF amplifier section.

It may be that a predetermined reference DC voltage supplied for removing influence of a DC potential of the IF amplifier section inputted to each Gm amplifier of the RSSI amplifier section is made by a semi-circuit of the IF amplifier section and is supplied from a node corresponding to a signal output terminal of the IF amplifier section.

The rectification circuit for rectifying an output current of the RSSI amplifier section may be arranged so as to double as a base current compensation circuit for the current mirror circuit.

The RSSI circuit may be arranged so that an output load resistor of the RSSI voltage output section for converting into a voltage by flowing the output current from a rectification circuit is formed within an LSI, and this resistor is of the same kind as a reference resistor used for forming a current source for the RSSI amplifier section, and thereby resistance depending characteristics of Gm amplifier generated in the RSSI amplifier section is canceled when a current-voltage conversion is performed in the RSSI voltage output section.

The RSSI circuit may be arranged so as to include a temperature correction circuit for applying a minute current directly proportional to absolute temperature to a resistor of the current-voltage conversion circuit of the RSSI voltage output section, so as to correct the temperature error of the RSSI output voltage.

The RSSI circuit may be arranged so that a load resistor of the IF amplifier section, an output load resistor of the rectification circuit, and a resistor for making a current source are of the same kind (having the same specification characteristics, particularly, the same temperature characteristics specification value), and a correction current outputted from the temperature correction circuit has the same source as the current source for amplifying electricity of the IF amplifier section.

The RSSI circuit may be arranged so that a current source for the IF amplifier section is made of a band gap current source, and a current source for the RSSI amplifier section is made by using as a current source a current which flows through a resistor to which a voltage is applied by the band gap current source.

The RSSI detection circuit of the present invention inputs an output of the RSSI circuit and a predetermined reference voltage into a comparator and outputs a digital signal. In this way, whether the value of inputted signal power is greater or smaller than a power value set by the arbitrary reference voltage can be detected and displayed.

Conventionally, the current supplied from the IF amplifier current source circuit 1210 varies depending on voltage Vt and inner resistance R. As such, an output from the IF amplifier circuit 1220 also varies depending on voltage Vt and inner resistance R. When the input level is low and accordingly the amplifiers 1221, 1222, 1223 and 1224 of the respective stages of the IF amplifier circuit 1220 do not saturate, these amplifiers do not have temperature dependence.

However, when the input level is high and accordingly the amplifiers 1221, 1222, 1223 and 1224 of the respective stages of the IF amplifier circuit 1220 saturate sequentially from a later stage to a previous stage, the output from each of the amplifiers 1221, 1222, 1223 and 1224 becomes the product of the load resistors 1321 and 1322 and a current from the current source 1328, and shows high (strong) temperature dependence directly proportional to Vt (Vt=kT/q; here, k is a Boltzmann constant, T is absolute temperature, and q is an amount of electrical charge).

Here, the RSSI amplifier circuit 1230 outputs a current directly proportional to the magnitude of an inputted absolute value signal, but the output current in the saturated state is larger than that in the unsaturated state. Therefore, the temperature characteristic in the saturated state has dominant influence on the whole temperature characteristic. Therefore, in order to suppress the whole temperature characteristic, the temperature characteristic in the saturated state should be emphasized.

A signal output in the saturated state has the temperature characteristic directly proportional to absolute temperature. As such, when the temperature characteristic of the RSSI amplifier section is inversely proportional to absolute temperature, the temperature characteristics of the RSSI circuit can be cancelled as a whole, and accordingly the large temperature dependence can be suppressed. The rectification circuit removes a signal frequency component from the output current of the RSSI amplifier section, and thereby produces a DC current. The voltage produced by causing the output DC current of the rectification circuit to flow through a resistor or the like is obtained as an RSSI output voltage.

Here, because a temperature characteristic correction error in the unsaturated state still remains in this RSSI voltage, a minute correction current directly proportional to absolute temperature is applied to the RSSI output section so as to reduce the correction error. By applying the correction current, the temperature dependence of the RSSI output voltage in the saturated state increases, and the temperature dependence of the RSSI output voltage in the unsaturated state decreases. Therefore, by applying a suitable correction current, the temperature dependence in an operational range is improved as a whole.

To be specific, the temperature characteristic of the circuit as a whole is controlled by taking into consideration the temperature characteristic of Vt, the temperature characteristic of the resistor, and the temperature characteristic of the reference voltage, which are the main cause of the change in temperature characteristic. In regard to a change of performance caused by the Vt temperature characteristic, two kinds of current sources, one which depends on Vt and one which does not depend on Vt are used, and an amplifier whose characteristics are inversely proportional to Vt is used when the current source does not have temperature dependence. In this way, a temperature characteristic of the RSSI circuit system is controlled as a whole.

Further, the current source is formed based on a current generated by applying a voltage to the reference resistor, and a load resistor with the same characteristics as the reference resistor is used, so as to cancel the temperature characteristic caused by the resistors. As a result, the temperature characteristic of the RSSI circuit system is controlled as a whole. Further, a portion of the IF amplifier circuit is used for the bias circuit used for an RSSI reference voltage, so that a differential input of the RSSI amplifier input section is balanced and accordingly temperature dependence error of DC voltage is removed.

As described above, in regard to the temperature characteristic in the saturated state of the IF amplifier section, the opposite temperature characteristic are given to the RSSI amplifier section, so that the temperature characteristics of the both can be cancelled. By thus canceling the temperature characteristics, the RSSI circuit can suppress the temperature dependence.

Further, in the RSSI circuit, as for a remaining temperature error, by applying a minute current directly proportional to absolute temperature, temperature dependence can be reduced within an operational range to such an extent that it is negligible. Therefore, with the simple circuit, a temperature characteristic can be corrected with high accuracy.

In an actual circuit, a temperature error caused by the temperature dependence of Vt, the resistor and the bias are generated. However, the temperature characteristics of Vt and R can be cancelled by connecting, with the circuit, a circuit having the opposite characteristics. Further, by completely synchronizing a change of a DC voltage of the differential input with a change of a signal source DC voltage, changes of the DC voltages can be cancelled and accordingly the temperature dependence can be suppressed As a result, the temperature correction circuit can be realized with a simple circuit, and the temperature correction circuit and the current source of the amplifier can use most parts in common, so that consumption of current can be reduced and the circuit can be downsized.

INDUSTRIAL APPLICABILITY

An RSSI circuit of the present invention can suppress a change of characteristics due to a temperature change. Thus, when used in an RSSI detection circuit or a wireless receiver, the RSSI circuit can accurately measure strength of a received signal. With the high temperature stability, the RSSI circuit can suitably adjust strength of an IF signal obtained from the received signal. As a result, demodulation from the received signal can be performed more reliably, and reception characteristics can be increased as a result. Therefore, the RSSI circuit can be suitably used in the fields of communications.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A received signal strength measurement circuit comprising:
    an IF amplifier section, which includes multiple stages of serially connected differential amplifiers for amplifying, with use of a first current source provided as a power source for amplification, an IF signal corresponding to a received signal;
    a voltage-current conversion section for converting into current a voltage amplitude of an absolute value signal outputted from the differential amplifier of each stage of the IF amplifier section, using a second current source provided as a power source for conversion, and adding and outputting the converted current; and
    a voltage output section for converting into voltage the output current from the voltage-current conversion section, and outputting the converted voltage as a measurement voltage value,
    the voltage-current conversion section being set so that a current value of the voltage-current conversion is inversely proportional to absolute temperature.

2. The received signal strength measurement circuit as set forth in claim 1, wherein
    said differential amplifier comprises a pair of first transistors whose emitters are connected with each other, and load resistors respectively connected between collectors of the first transistors and a power source, and said differential amplifier outputs an emitter voltage of the first transistors as the absolute signal, and
    said first current source is connected with the emitters of the first transistors, includes a reference resistor for regulating an output current of the first current source, and outputs a current whose value is inversely proportional to the reference resistor, the reference resistor having the same temperature characteristic as the load resistors to cause the output current to be directly proportional to absolute temperature.

3. The received signal strength measurement circuit as set forth in claim 1, wherein
    said voltage-current conversion section includes a differential amplifier for converting into current a voltage amplitude of an absolute signal outputted from the differential amplifier of each stage of the IF amplifier section,
    said differential amplifier of the voltage-current conversion section includes a pair of second transistors whose emitters are connected with each other, and a current mirror circuit whose input is connected with one of collectors of the second transistors and whose output is connected, as an active load, with the other collector of the second transistors, the output of the current mirror circuit being provided as an output of the voltage-current conversion section, and
    said second current source is connected with the emitters of the second transistors, and an output current value of the second current source is set to reduce temperature dependency, so as to cause the output current from the differential amplifier of the voltage-current conversion section to be inversely proportional to absolute temperature.

4. The received signal strength measurement circuit as set forth in claim 3, further comprising a reference voltage forming circuit for generating a reference DC voltage, wherein the reference DC voltage and the absolute value signal are inputted to the differential amplifier of the voltage current conversion section, and the reference voltage forming circuit is identical in circuit structure with the differential amplifier of the IF amplifier section so as to remove influence of a DC potential included in the absolute value signal, and the reference voltage forming circuit supplies the reference DC voltage from a node corresponding to an output terminal for the absolute value signal.

5. The received signal strength measurement circuit as set forth in claim 3, further comprising a reference voltage forming circuit for generating a reference DC voltage, wherein the reference DC voltage and the absolute value signal are inputted to the differential amplifier of the voltage current conversion section, and the reference voltage forming circuit serves as a differential semi-circuit of the differential amplifier of the IF amplifier section so as to remove influence of a DC potential included in the absolute value signal, and the reference voltage forming circuit supplies the reference DC voltage from a node corresponding to an output terminal for the absolute value signal.

6. The received signal strength measurement circuit as set forth in claim 1, further comprising a rectification section for reducing an alternating current component of the output current from the voltage current conversion section, wherein the rectification section includes a current mirror circuit section, and a base current compensation circuit for the current mirror circuit section.

7. The received signal strength measurement circuit as set forth in claim 1, wherein an output load resistor of the voltage current conversion section is identical in specifications with a reference resistor used for the voltage-current conversion section.

8. The received signal strength measurement circuit as set forth in claim 1, wherein said voltage output section comprises a conversion resistor for converting a current into a voltage, said received signal strength measurement circuit further comprising a temperature correction circuit for generating a correction current to be applied to the conversion resistor, the correction current being generated to be directly proportional to absolute temperature and smaller than the current value of a first current source.

9. The received signal strength measurement circuit as set forth in claim 6, wherein a load resistor of the differential amplifier of the IF amplifier section is identical in specifications with an output load resistor of the rectification section.

10. The received signal strength measurement circuit as set forth in claim 8, wherein the temperature correction circuit is included in the first current source.

11. The received signal strength measurement circuit as set forth in claim 1, wherein the first current source includes a band gap current source, and the second current source is made by using as a current source a current which flows through a resistor to which a voltage is applied by the band gap current source.

12. The received signal strength measurement circuit as set forth in claim 1, wherein, in the differential amplifier of the IF amplifier section, the output voltage amplitude of the absolute value signal in a saturated state has temperature dependence directly proportional to absolute temperature, and the temperature dependence of the output voltage amplitude of the absolute value signal in an unsaturated state is smaller than that in a saturated state.

13. A received signal strength detection circuit comprising:

a received signal strength measurement circuit; and a comparator for outputting as a digital signal a result of comparison of an output voltage value of the received signal strength measurement circuit and a predetermined reference voltage, the received signal strength measurement circuit including:

an IF amplifier section, which includes multiple stages of serially connected differential amplifiers for amplifying, with use of a first current source provided as a power source for amplification, an IF signal corresponding to a received signal;

a voltage-current conversion section for converting into current a voltage amplitude of an absolute value signal outputted from the differential amplifier of each stage of the IF amplifier section, using a second current source provided as a power source for conversion, and adding and outputting the converted current; and a voltage output section for converting into voltage the output current from the voltage-current conversion section, and outputting the converted voltage as a measurement voltage value, the voltage-current conversion section being set so that a current value of the voltage-current conversion is inversely proportional to absolute temperature.

14. A wireless receiver comprising a received signal strength measurement circuit, the received signal strength measurement circuit including:

an IF amplifier section, which includes multiple stages of serially connected differential amplifiers for amplifying, with use of a first current source provided as a power source for amplification, an IF signal corresponding to a received signal;

a voltage-current conversion section for converting into current a voltage amplitude of an absolute value signal outputted from the differential amplifier of each stage of the IF amplifier section, using a second current source provided as a power source for conversion, and adding and outputting the converted current; and a voltage output section for converting into voltage the output current from the voltage-current conversion section, and outputting the converted voltage as a measurement voltage value, the voltage-current conversion section being set so that a current value of the voltage-current conversion is inversely proportional to absolute temperature.

15. A wireless receiver comprising a received signal strength detection circuit, the received signal strength detection circuit including a received signal strength measurement circuit and a comparator for outputting as a digital signal a result of comparison of an output voltage value of the received signal strength measurement circuit and a predetermined reference voltage, the received signal strength measurement circuit including:

an IF amplifier section, which includes multiple stages of serially connected differential amplifiers for amplifying, with use of a first current source provided as a power source for amplification, an IF signal corresponding to a received signal;

a voltage-current conversion section for converting into current a voltage amplitude of an absolute value signal outputted from the differential amplifier of each stage of the IF amplifier section, using a second current source provided as a power source for conversion, and adding and outputting the converted current; and a voltage output section for converting into voltage the output current from the voltage-current conversion section, and outputting the converted voltage as a measurement voltage value, the voltage-current conversion section being set so that a current value of the voltage-current conversion is inversely proportional to absolute temperature.

* * * * *